United States Patent [19]

Christie et al.

[11] 4,241,051
[45] Dec. 23, 1980

[54] CALCITONIN

[76] Inventors: Robert B. Christie, 49 Willingdon Park Dr., Hampden Park, Eastbourne, East Sussex; John A. Parsons, 17 Ovington St.; Christopher G. Rudman, 12 Lawrence Mansions, Lordship Pl., Cheyne Walk, both of London SW3, all of England

[21] Appl. No.: 955,608

[22] Filed: Oct. 30, 1978

[30] Foreign Application Priority Data

Nov. 4, 1977 [GB] United Kingdom ............... 45967/77

[51] Int. Cl.² ..................... A61K 37/00; C07C 103/52
[52] U.S. Cl. .............................. 424/177; 260/112.5 T
[58] Field of Search .................. 424/177; 260/112.5 T

[56] References Cited

FOREIGN PATENT DOCUMENTS 1354525 4/1971 United Kingdom ..................... 424/177

OTHER PUBLICATIONS

Gaucher, Revue du Rhumatisme, 1975, 42,595.
Editorial, British Medical Journal, 1977, No. 60741427.
Menzies et al., Acta Otolaryngal 1975, 79, 378.
Solomon et al., BMJ, 1977, 2, 485.
Foster et al., Oral Surgery, 1974, 38, 866.
Yegorov, Oftalmol Zhurnal, 1976, 31, 454.
McDavid, et al., Dental Research, 1977, 56, 540.

Primary Examiner—Delbert R. Phillips
Attorney, Agent, or Firm—Leon E. Tenenbaum

[57] ABSTRACT

A method for the treatment of pathological processes in bone and connective tissue comprises the topical application of calcitonin to effect control of said processes by transepithelial action. Preferred compositions for use in the method are ear drops comprising an aprotic solvent or an aqueous medium containing a surface active agent.

10 Claims, 2 Drawing Figures

CALCITONIN

FIELD OF THE INVENTION

This specification relates to pharmaceutical compositions and more particularly to compositions for the control of pathological processes in bone and connective tissue.

DESCRIPTION OF THE PRIOR ART

Calcitonin is one of the hormones involved in the control of calcium metabolism in the body. Recently there have been reports of the beneficial effect of calcitonin on Pagetic involvement of the ossicles when it is given systemically for Pagets' disease (specific details of this and other art are to be found in the accompanying Prior Art Statement). However, the value of calcitonin in such a context is limited by the mode of administration as the systemic administration of a hormone is difficult to justify as a general procedure for the treatment of localised conditions, for example otosclerosis which is far more prevalent than Pagetic involvement of the ossicles.

We have now discovered that, quite contrary to what would be expected from the molecular size and peptide nature of calcitonin and its normal mode of distribution by the bloodstream and inactivation by proteases, calcitonin may be administered topically to achieve a high degree of efficacy directly by transepithelial action. Such a form of administration is very useful, inter alia, for the treatment of conditions such as otosclerosis.

SUMMARY OF THE INVENTION

According to the present invention a method for the treatment of pathological processes in bone and connective tissue, for example in mammals and particularly in human patients, comprises the topical application of calcitonin (as hereinafter defined) to effect control of said processes by transepithelial action.

By the term "calcitonin" as used herein is meant not only peptides having a structure corresponding to one of the naturally occurring hormones, and which may be naturally or synthetically produced, but also related synthetic peptides having calcitonin activity.

DETAILED DESCRIPTION OF THE INVENTION

Figure 1:
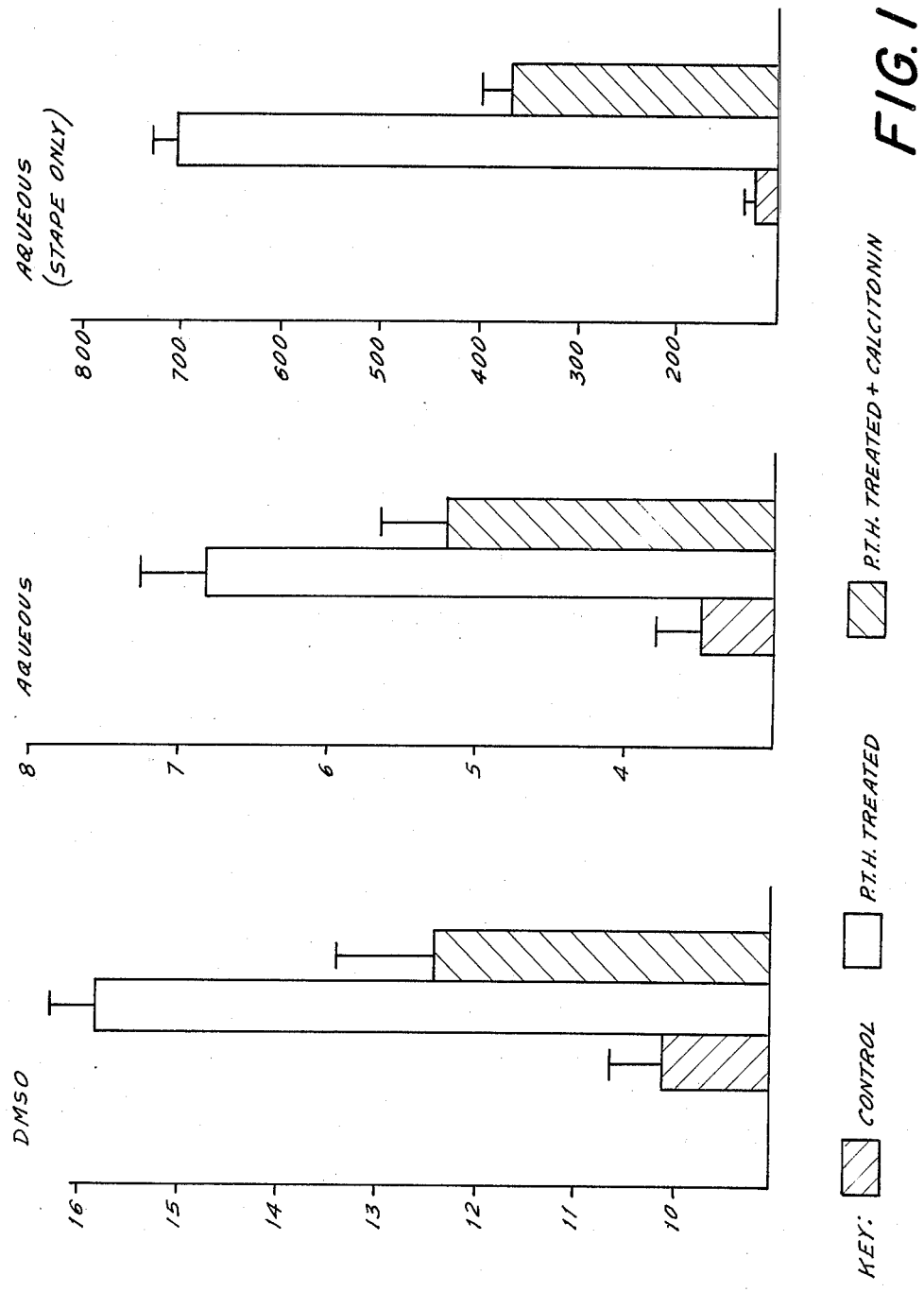
Figure 2:
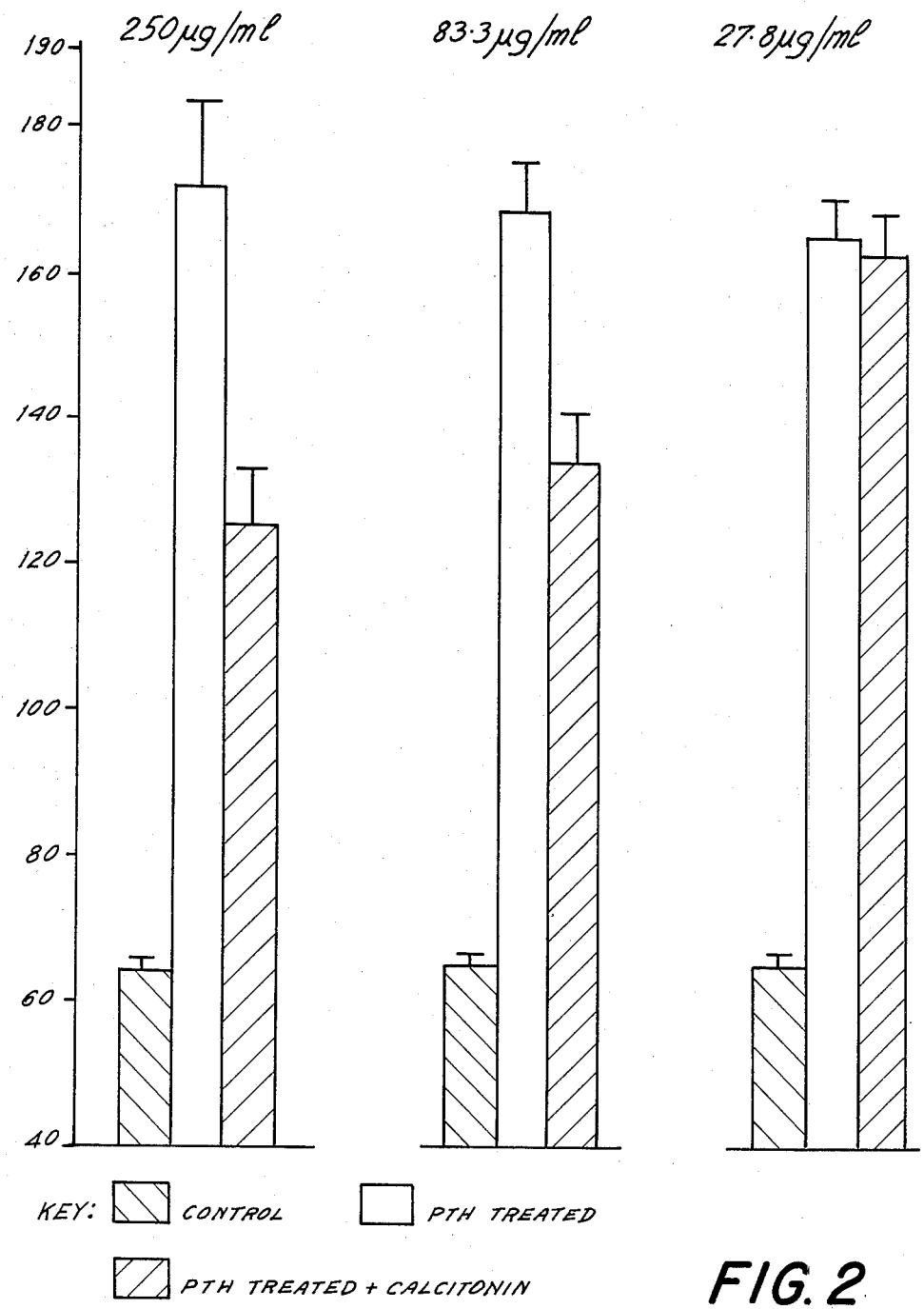

The specification is accompanied by FIGS. 1 and 2 which illustrate the effects produced by the method of the invention and are described in detail in the Examples.

All of the peptides at present known to exert potent calcitonin activity comprise approximately thirty two amino acid residues, of which the seven at the amino terminal end of the peptide chain are held in a cyclic configuration by a sulphur or carbon bridge and the carboxyl terminal residue consists of proline amide. The detailed structure within the peptide chain of the hormone varies among different species and whilst the hormones, and their derivatives and analogues, found in various species are of interest for use in the present invention, for example the human and porcine calcitonins, the eel and particularly salmon calcitonins are of special interest in view of their relatively hydrophobic character and their particular stability.

Calcitonin may be formulated in various ways for use in the method of the present invention, the nature of the composition used depending particularly upon the site of the topical administration. The invention is of particular value in relation to the administration of calcitonin to the skin using suspensions, emulsions and particularly solutions.

One area of transepithelial, or transdermal, administration of especial interest is administration into the ear in the form of ear drops for the control of pathological ossification of the ossicles. The ear drops may be sterile, although this need not necessarily be the case, and they usually contain calcitonin in suspension or preferably in solution. The diluent used in the ear drops may be non-aqueous or aqueous. In the former instance the preferred group of diluents is the physiologically acceptable aprotic polar solvents. Preferred compounds of this type are those with which it is possible to produce, if not complete solution, at least a solution of adequate concentration of dissolved calcitonin rather than a suspension with little actual solution, for example compounds such as dimethylsulphoxide, dimethyl formamide and dimethyllauramide etc, rather than compounds such as propylene carbonate. Other groups of non-aqueous diluents of some interest are the polyhydroxy alcohols such as glycerol, propylene glycol, etc and oils such as the vegetable oils, for example olive oil. If desired, such non-aqueous media may be mixed with water to form the diluent of the composition. However, the degree of physiological acceptability of the non-aqueous diluents is generally somewhat less than that of aqueous media and this is especially the case with the aprotic polar solvents. A preferred diluent is therefore water without the addition of organic solvents. In order to aid flow of the drops into the ear and possibly also the absorption of the calcitonin, an aqueous medium conveniently also comprises a physiologically acceptable surface active agent. The amount of such an agent may conveniently be in the range from 0.01 to 0.5% w/v the aqueous composition although the amount is in general kept as low as possible and an amount in the range of from 0.05 to 0.15% w/v, for example 0.1% w/v is generally preferred. Such agents may be cationic, anionic, or non-ionic or a mixture of two or more of these and may be selected among the agents described below with due regard to physiological acceptability.

Agents of the cationic type include long chain amine condensates with ethylene oxide and quaternary ammonium compounds, for example cetyl trimethyl ammonium bromide and dodecyl dimethyl ammonium bromide. Suitable anionic agents include soaps, salts of aliphatic monoesters of sulphuric acid, for example sodium lauryl sulphate and sodium heptadecyl sulphate, sulphonated aromatic compounds, for example alkyl benzene sulphonic acids and salts thereof such as tridecylbenzene sulphonic acid and the sodium and amino salts of dodecylbenzene sulphonic acid, alkyl napthalene sulphonates such as sodium butylnapthalene sulphonate, sulphosuccinates such as sodium dioctyl sulphosuccinate, and N-acyl-N-alkyl fatty acid taurates.

Non-ionic agents include (a) ethoxylated alkylphenols (b) ethoxylated aliphatic alcohols, (c) carboxylic esters and (d) carboxylic amides, as described hereinafter.

(a) The ethoxylated alkyphenon non-ionic surface active agents include various polyethylene oxide condensates of alkylphenols, especially the condensation products of mono-alkylphenols or di-alkylphenols wherein the alkyl group contains about 6 to about 12 carbon atoms in either branched chain or particularly straight chain configuration, for example octyl cresol, octyl phenol or nonyl phenol, with ethylene oxide, the said ethylene oxide being present in amounts equal to from about 5 to about 25 moles of ethylene oxide per mole of alkylphenol.

(b) One particular type of ethoxylated aliphatic alcohol non-ionic surface active agents is the condensation products of aliphatic alcohols having from about 8 to 18 carbon atoms in either straight chain or branched chain configuration, for example oleyl or cetyl alcohol, with ethylene oxide, the said ethylene oxide being present in equal amounts of from about 30 to about 60 moles of ethylene oxide per mole of alcohol.

(c) Particular types of carboxylic ester non-ionic surface active agents are firstly the partial, for example mono-, esters formed by the reaction of fatty and resin acids, for example of about 8 to about 18 carbon atoms, with polyhydric alcohols, for example glycerol, glycols such as mono-, di-, tetra- and hexaethylene glycol, sorbitan, etc; and similar compounds formed by the direct addition of varying molar ratios of ethylene oxide to the hydroxy group of fatty acids.

A second type of carboxylic esters is the condensation products of fatty and resin acid partial, for example mono-, esters with ethylene oxide, such as fatty or resin acid esters of polyoxyethylene sorbitan and sorbitol, for example polyoxyethylene sorbitan mono-tall oil esters. These may contain, for example, from about 3 to about 80 oxyethylene units per molecule and fatty or resin acid groups of from about 8 to about 18 carbon atoms. Examples of naturally occurring fatty acid mixtures which may be used are those from coconut oil and tallow whilst examples of single fatty acids are dodecanoic acid and oleic acid.

(d) One particular type of carboxylic amide non-ionic surface active agents is the ammonia, monoethanol and diethanol amides of fatty acids having an acyl chain of from about 8 to about 18 carbon atoms.

Among the above described surface active agents, the non-ionic and particularly the anionic agents are of especial interest and the sulphosuccinates, for example sodium dicoctyl sulphosuccinate, and related agents have proved to be of particular value. The ear drops may also contain other additives, if desired, including proteins such as gelatin and albumin to aid the complete transfer of the aqueous calcitonin from its container, compounds such as hydrocortisone to lessen any possible allergic effects, and compounds to stabilise the compositions for storage, for example anti-oxidants in the case of human and related calcitonins containing a methionine residue adjacent to the N-terminal cyclic group of seven residues.

Alternative forms of composition to ear drops include ointments, which are of particular value for the administration of calcitonin to joints for the control of osteoporosis by transdermal action. Such ointment may conveniently comprise carriers of the type used in the art for compositions of this type containing other active ingredients.

It will be appreciated from the foregoing description that the present invention also comprises a novel form of pharmaceutical composition for the treatment of pathological processes in bone and connective tissue of the ear which comprises a medium suitable for administration as ear drops and containing a therapeutically effective amount of calcitonin, said medium comprising an aprotic solvent or an aqueous medium containing a surface active agent.

The amount of calcitonin contained in the compositions may vary according to various parameters such as the nature of the composition, including the particular calcitonin contained therein, and the site of application, etc. However, the concentrations are often somewhat higher than those found in compositions for the systemic administration of calcitonin, being for example as much as 250 micrograms per ml, although lower amounts may also be used. Indeed, in view of the relatively high cost of calcitonin, it is particularly preferred to reduce the amount administered in as far as possible. It has been found, however, that a concentration level of greater than about 25 micrograms per ml is generally required to achieve an adequate effect, for example about 30 or 40 micrograms per ml and especially at least 50 or 60 micrograms per ml, and a concentration in the range from 80 to 250 micrograms per ml is often employed. The calcitonin may be formulated in unit dosage form but this is often not the case in view of the method of administration.

The levels of administration of calcitonin also vary somewhat from those used systemically. In the case of human patients, for example, amounts of from 0.7 to 70 micrograms, particularly from 2.5 to 25 micrograms, are usually appropriate for single dosages given at a particular site and repeated if necessary, and such dosages correspond generally to about 0.01 to 1 micrograms, and particularly 0.03 to 0.3 micrograms, per kilogram of body weight. (The above concentration and dosage levels of calcitonin apply to calcitonin with a potency of about 4500 International units per mg and may be adjusted pro rata for calcitonin of other potencies.)

As indicated above, a particular application of the invention is for the control of pathological ossification in the ear. It has been found that introduction of calcitonin into the ear in the form of ear drops is effective in controlling hormone-induced pathological processes in the ossicles, including the stapes which is furthest removed from the site of topical application. Such a procedure provides a considerable advance in the treatment of otosclerosis and other conditions affecting the ossicles which at present are usually dealt with by surgery.

The invention is illustrated by the following Examples.

EXAMPLE 1

A large dose of radio calcium (400 $\mu$Ci of $^{45}$Ca) is administered intravenously to each of eight guinea pigs to label their skeletons. On the third, fourth and fifth days after administration of the radiocalcium each of the guinea pigs receives ear drops containing a solution of synthetic salmon calcitonin (Armour Pharmaceutical Co.) dissolved in dimethylsulphoxide (0.1 ml of solution containing 25$\mu$g of calcitonin). Four of the animals receive calcitonin to the right ear and four to the left ear, 0.1 ml of dimethylsulphoxide being given to the other ear in each case as a control.

One hour before sacrifice on the fifth day three animals from each group of four are treated intravenously with 500 MRC units of bovine parathyroid hormone (bPTH; 2000U/mg) in diluted plasma to stimulate bone resorption, the remaining animal in each group receiving diluted plasma only as a control. After sacrifice in alternation by ether anaesthesia, the ossicles of each ear of each animal are removed by the opening the temporal bone from its lower surface, remote from the external ear to which calcitonin has been applied. They are explanted onto a filter disc (Millipore HA) in a tissue culture dish containing 1 ml of the Fitton-Jackson modification of BGJ (Gibco-Biocult Ltd) with added ascorbic acid (150 µg/ml), streptomycin (5 mg/100 ml) and penicillin (5000U/100 ml), gassed with 93% air, 7% carbon dioxide. The bathing medium is withdrawn from each dish after 20, 40 and 60 hours incubation in an airtight container at 37° C. and is replaced with freshly gassed medium. After addition to 4 ml aliquots of scintillator (Packard Instagel) the samples are subjected to liquid scintillation spectrometry (Packard 2425 set to the $^{14}C$ channel).

In a variation of the procedure described above, the calcitonin is administered in 0.1% w/v aqueous sodium dioctyl sulphosuccinate rather than in dimethyl sulphoxide in two separate experiments, the whole of the ossicles being explanted as described above in the first case and only the stapes being explanted in the second. In these two experiments some variation is made in the radiolabelling procedure, only 200 µCi of $^{45}Ca$ being given in the first case but intraperitoneally rather than intravenously to facilitate the labelling of bone and 400 µCi of $^{45}Ca$ being given in the second case, also intraperitoneally, but with omission of the methyl red from the BGJ culture medium as this causes considerable quenching.

It is typically found that for all procedures successive samples of the culture fluid all show concentrations of radiocalcium which increase progressively from 20 to 60 hours. The rates of increase are closely similar, which suggests that the resorptive processes, already determined at the time of explantation, continue with little change during culture. Differences in the observed radiocalcium concentration caused by various treatments are similar at all three sampling times. Typical results obtained at the 40 hour readings are illustrated in the Figure, the radio activity released into the bathing medium during the second 20 hour period being indicated by the ordinate scale (as $cpm \times 10^{-3}/gm$ bone, mean+SEM). The first bar of each set shows the release of $^{45}Ca$ from ossicles of the ear which received eardrops without any calcitonin content in animals which received no bPTH. The second and third bars of each set show the release of $^{45}Ca$ from ossicles of the bar which received eardrops without calcitonin and with calcitonin, respectively in animals which received bPTH. It will be seen that in each of the three cases, the antagonism by calcitonin of the bPTH-stimulated resorption was highly significant ($p<0.01$ in the experiments where the whole of the ossicles was explanted and $p<0.005$ in the experiment where only the stapes were explanted).

EXAMPLE 2

A group of twenty-four guinea pigs is treated as described in Example 1 to effect labelling of their skeletons, a dose of 400 µCi of $^{45}Ca$ being given intraperitoneally. The animals are then divided into three groups which are treated as described in Example 1 with 0.1 ml of a solution of concentration 27.8 µg/ml, 83.3 µg/ml or 250 µg/ml of synthetic salmon calcitonin in 0.1% w/v aqueous sodium dioctyl sulphosuccinate. The subsequent treatment of the animals follows that of Example 1, the methyl red being omitted from the BGJ culture medium.

The bathing medium from the cultures is examined after 20, 40 and 60 hours. It is typically found that the doses of 83.3 µg/ml and 250 µg/ml are of a very similar level of effect whilst the 27.8 µg/ml dose has little effect. As in Example 1, it is typically found that the effect is a continuing one during the period of culture suggesting that an application of the calcitonin in vivo produces an effect of extended duration. Typical results obtained at the 40 hour reading are illustrated in FIG. 2 in a similar fashion to FIG. 1.

We claim:

1. A method for the treatment of a patient suffering from pathological processes in bone and connective tissue of the ear which comprises the topical application of calcitonin (as hereinbefore defined) to effect control of said processes by transepithelial action at the site of application.

2. A method according to claim 1, wherein the patient is suffering from osteoporosis.

3. A method according to claim 1, wherein the patient is suffering from otosclerosis, the treatment being by means of ear drops.

4. A method according to claim 3, wherein the ear drops comprise an aprotic solvent containing a therapeutically effective amount of calcitonin.

5. A method according to claim 3, wherein the ear drops comprise an squeous medium containing a surface active agent and a therapeutically effective amount of calcitonin.

6. A method according to claim 3, wherein the calcitonin is a fish calcitonin.

7. A pharmaceutical composition for the treatment of pathological processes in bone and connective tissue of the ear which comprises a medium suitable for administration as ear drops and containing a therapeutically effective amount of calcitonin (as hereinbefore defined), said medium being selected from the group consisting of an aprotic solvent and an aqueous medium containing a surface active agent.

8. A pharmaceutical composition according to claim 7, wherein the medium is dimethylsulphoxide, dimethyl formamide or dimethyl lauramide.

9. A pharmaceutical composition according to claim 7, wherein the medium is an aqueous medium containing an anionic surface active agent.

10. A pharmaceutical composition according to claim 9, wherein the anionic surface active agent is sodium dioctyl sulphosuccinate.

* * * * *